United States Patent [19]

Babayan et al.

[11] Patent Number: 4,847,296

[45] Date of Patent: Jul. 11, 1989

[54] TRIGLYCERIDE PREPARATIONS FOR THE PREVENTION OF CATABOLISM

[76] Inventors: Vigen K. Babayan, 178 Beethoven Ave., Waban, Mass. 02168; George L. Blackburn, 241 Perkins, Jamiaca Plains, Mass. 02130; Bruce R. Bistrian, 189 Argilla Rd., Ipswich, Mass. 01938

[21] Appl. No.: 28,278

[22] Filed: Mar. 20, 1987

Related U.S. Application Data

[63] Continuation-in-part of Ser. No. 897,446, Aug. 15, 1986, abandoned, which is a continuation of Ser. No. 650,771, Sep. 13, 1984, abandoned.

[51] Int. Cl.[4] .............................................. A61K 31/23
[52] U.S. Cl. .................................................... 514/552
[58] Field of Search ...................... 514/552; 424/195.1

[56] References Cited

U.S. PATENT DOCUMENTS

| | | | |
|---|---|---|---|
| 4,423,072 | 12/1983 | Stahly | 514/552 |
| 4,401,657 | 8/1983 | Kashiwabara et al. | 514/2 |
| 4,528,197 | 7/1985 | Blackburn | 514/552 |

OTHER PUBLICATIONS

Technical Bulletins "Captex 710 A", on Captex 810 B.
Chem. Abst. 100:190682c, 1984.

*Primary Examiner*—John W. Rollins
*Attorney, Agent, or Firm*—Gerald D. Sharkin; Robert S. Honor; Walter F. Jewell

[57] ABSTRACT

Chemically synthesized structured triglycerides (lipids) for enteral administration as the lipid calorie source, is subjects undergoing severe metabolic stress.

13 Claims, 2 Drawing Sheets

TRIGLYCERIDE PREPARATIONS FOR THE PREVENTION OF CATABOLISM

This application is a continuation-in-part of application Ser. No. 897,446 filed Aug. 15, 1986, now abandoned, which application is a continuation of application Ser. No. 650,771 filed Sept. 13, 1984, now abandoned.

This invention relates to triglyceride preparations for enteral administration to prevent catabolism and to increase protein synthesis in subjects undergoing severe metabolic stress.

Under normal nutritional and physiological conditions, fuel requirements of the body are largely met by glucose and fatty metabolism. The body's amino acids generally contribute little towards overall fuel economy at these times. However, during abnormal metabolic stress states induced by trauma or sepsis, fat mobilization and utilization and glucose utilization are relatively decreased due to hormonal changes precipitated by the stress. Under these conditions, an extremely high and rapid rate of muscle protein catabolism occurs.

Over the last several years, investigators have studied the metabolic consequences of trauma in man. Most of these studies concerned themselves with understanding cause and effect, as it related to biochemistry and metabolism, and subsequent physiological responses. Investigators have found for example that large (e.g. 25%) body surface area burns increase basal energy expenditure as much as two fold. The release rate of peripheral amino acids also increases approximately 3–4 times under similar traumatic conditions. These changes, if persistent, may result in protein malnutrition, alterations in essential organ functions, and, finally, multiple organ failure. For these reasons most clinicians have recommended intensive nutritional therapy for the severely injured or burned patient.

Wilmore D. W. "Panel Report on Nutritional Support of Patients with Trauma or Infection", Am. J. Clin. Nutr., 34: 1213-22, 1981, has suggested that exogenous glucose administration at intakes exceeding energy expenditure may be of little benefit in severely stressed patients. An already abundant supply of glucose is present in these patients due to their hyperglycemic state. Elevated insulin levels associated with the hyperglycemia appear to reduce the availability of free fatty acid by limiting lipodysis.

Wannenmacher, R. W., Kaminski, M. V., "Use of Lipid Calories During Pneumoccal sepsis in the Rhesus Monkey. J.P.R.N. Nut. 6: 100-105, 1982, have suggested the energy needs of stressed patients may be optimally provided when fat is incorporated into the parenteral regimen. However, controversy exists over the value of lipid emulsions because their use has been implicated in Reticulo Endothelial System (RES) system blockage, increased prostaglandin production and development of Acute Respiratory Distress Syndrome (ARDS). These complications have been thought to be a result of reduced clearance of lipid chylomicrons as well as the high percentage of polyunsaturated fatty acids and arachidonic acid precursors in the lipid source.

Moreover, controlled trials in injured laboratory animals with triglyceride emulsions containing medium chain fatty acids exclusively, have failed to show any benefit for sparing body protein although the RES blockage is minimized by MCT emulsion over current long chain triglyceride emulsions.

This invention provides medium chain and long chain fatty acids chemically synthesized into structured triglycerides (lipids) for enteral administration as the lipid calorie source, in subjects undergoing severe metabolic stress.

The structured lipids of this invention have a random distribution of medium chain fatty acids ($C_{6-12}$ acid) and long chain fatty acids ($C_{14-24}$ acid). They may be represented by the following formula,

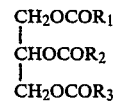

Wherein $R_1$, $R_2$, and $R_3$ may be independently a $C_6$ to $C_{24}$ acid, provided that one of $R_1$, $R_2$ or $R_3$ is a $C_{12}$ acid, and one of $R_1$, $R_2$ or $R_3$ is omega 6 or omega 3 acid such as, $C_{18}''$ or a $C_{18}'''$ acid.

$C_{18}''$ and $C_{18}'''$ represent the number of double bonds in the fatty acid moiety being one, two and three double bonds respectively.

The structured lipids of this invention may in general be prepared by any suitable process known in the art such as direct esterification, rearrangement, transesterification, displacement and the like. For example, the structured lipids may be prepared by the rearrangement of a vegetable oil such as coconut oil with a long chain triglyceride oil such as soybean oil.

The medium chain fatty acids used in the preparation of the structured lipids of this invention may be obtained from a vegetable oil such as kernel oils having a high lauric ($C_{12}$) acid content. Such oils include balassu oil, coconut oil, cohune oil, palm kernel oil, tucum oil and fractions thereof. The preferred vegetable oil is coconut oil.

The long chain fatty acids used in the preparation of the structured lipids of this invention may be polyunsaturated vegetable oils such as, corn oil, peanut oil, safflower oil, soybean oil, sunflower seed oil, and fish oils. The preferred long chain triglyceride oils are safflower oil, soybean oil, and sunflower seed oil.

Preferably, the percent composition mixtures of medium chain triglyceride oil to long chain triglyceride oils used in the preparation of the structured lipids of this invention may be 70 to 30%, 80 to 20%, 85 to 15%, or 90 to 10%. The 80 to 20% and the 85 to 15% mixtures are most preferred.

Typically, the structured lipids of this invention may be prepared from mixtures of coconut oil and soybean oil, which lipids may have the following fatty acid carbon chain length (CCL) composition.

| CCL | COCONUT OIL | SOYBEAN OIL | 100% | 80% 20% |
|---|---|---|---|---|
| $C_6$ | .67 | — | | .56 |
| $C_8$ | 9.91 | — | | 8.12 |
| $C_{10}$ | 6.48 | — | | 5.33 |
| $C_{12}$ | 45.82 | — | | 36.73 |
| $C_{14}$ | 17.63 | .05 | | 14.09 |
| $C_{16}$ | 8.66 | 10.25 | | 8.86 |
| $C_{18}$ | 2.66 | 4.45 | | 2.98 |
| $C_{18}'$ | 6.32 | 22.09 | | 9.27 |
| $C_{18}''$ | 1.84 | 53.96 | | 2.23 |
| $C_{18}'''$ | — | 8.30 | | 1.65 |
| $C_{20}$ | — | .21 | | .12 |

| | -continued | | |
|---|---|---|---|
| $C_{22}$ | — | .43 | .06 |

The present invention provides enteral preparations for use in stressed patients to prevent catabolism and to increase protein synthesis. The preparations provide from about 15 to 85% of the fat calories required in the stressed patient.

Typically, the compositions of this invention provide in a 70 Kg man, from about 0.3 gms of fat/Kg of body weight/day to about 4.0 gms of fat/Kg of body weight/day.

The lipid compositions are preferably administered with additional amino acids, vitamins and minerals as required. Modified amino acid formulas specifically designed for stressed subjects are preferred. The amino acids, vitamins and minerals can be administered in the same solution as the structured lipids or separately. It is preferred that the component groups be separately packaged to facilitate tailoring the diet to the patients specific needs.

In addition to the above, the formulations may include preservatives or stabilizers, as required.

The following examples further illustrates the present invention but are not meant to be limiting.

EXAMPLE I

In this example, a structured lipid preparation of this invention is compared with a medium chain lipid, and a long chain lipid for the oxidation of lipids in traumatized animals.

In this test, 18 male Sprague-Dawley rats were housed in suspension cages and allowed free access to food and water. When a proper weight of 200 grams was attained, the animals received a 25% full thickness scald burn on the dorsum for 15 seconds, under diethyl ether anesthesia. The rats were then returned to their cages and fasted overnight, but allowed to drink tap water ad libitum. On the day of the study, the animals were randomized into one of three groups to receive a 25 Kcal/Kg body weight intragastric bolus injection of lipid containing 5 u Ci (microcuries) of labeled oil.

Group I: a 20% medium chain lipid emulsion composed of 72.5% capric acid (C 8:0) and 27.5% coprylic acid (C 10:0) (obtained from Travenol Laboratories, Inc; Deerfield, Ill.).

Group II: a 20% long chain triglyceride emulsion (20% Travamulsion ®, Travenol Laboratories)

Group III: a 20% lipid emulsion composed of structured triglycerides obtained by rearrangement from 80% coconut oil and 20% soybean oil. Captex 710A Lot No. KH4022A (Capital City Products Co., Columbus, Ohio)

Immediately following the bolus administration of the lipid source, the rats were placed in metabolic chambers that permitted the collection and analysis of their expired breath. At 15 minute intervals for twelve hours, the specific activity of expired carbon dioxide was determined. At the end of the study, the animals were sacrificed.

Figure 1:
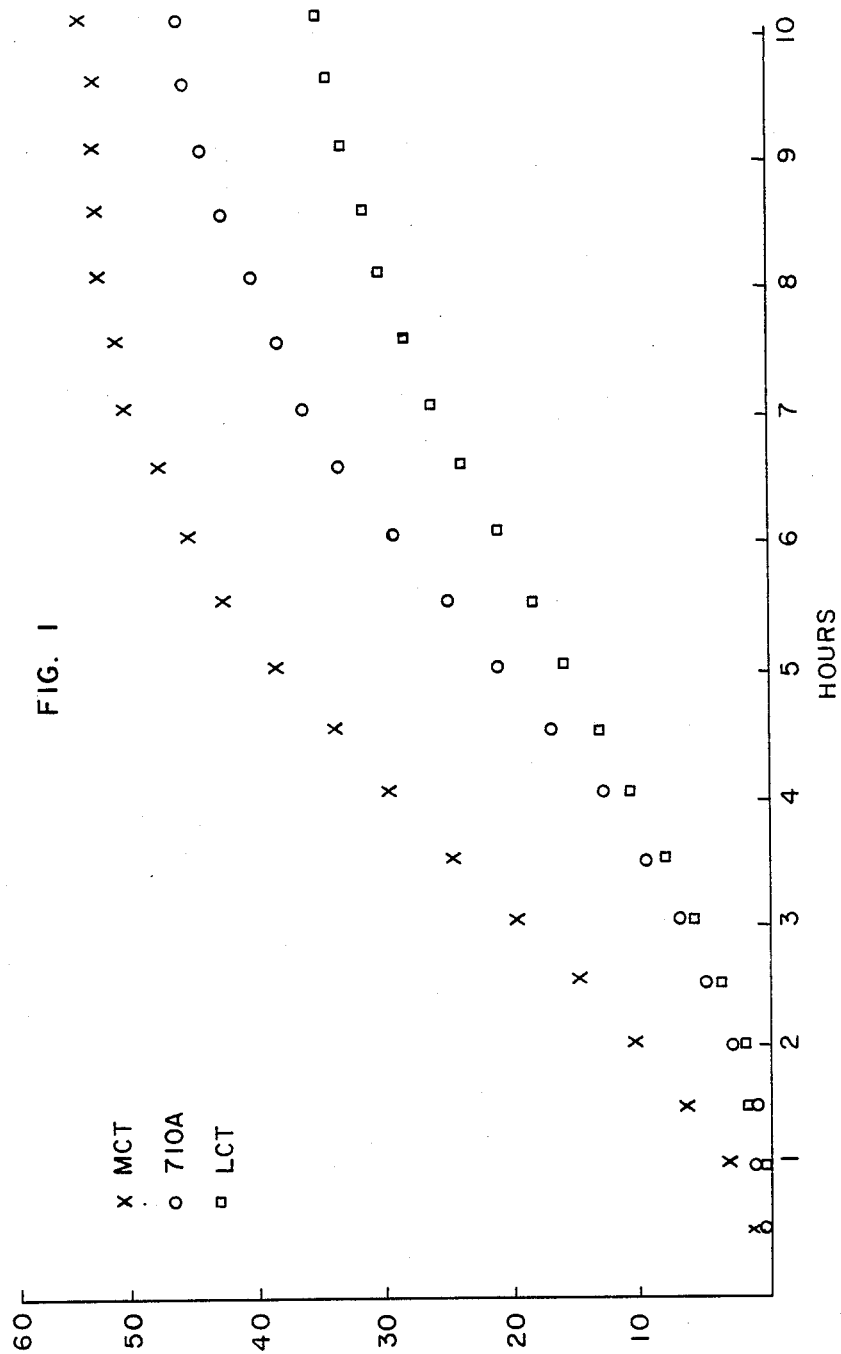
FIG. 1 is a comparison of the oxidation rate of medium chain triglyceride (MCT), a structured lipid of this invention (710A), and a long chain triglyceride (LCT)

The results are shown in FIG. 1. This shows the appearance of $C^{14}O_2$ after intragastric administration of 3.0 gm/Kg of fat in stressed rats. The results are an average of 6 rats per group.

The results show the structured lipids of this invention have an oxidation rate that falls between the medium chain triglycerides and the long chain triglycerides. Such structured lipids should be preferable and suitable for both enteral and parenteral nutrition.

EXAMPLE II

In this example, a structural lipid (SL) preparation of this invention (Captex 710A) was compared with a medium chain lipid (MCT), and a long chain lipid (LCT), for the effect of total enteral nutrition on protein metabolism in thermally injured rats.

In this test, 27 male Sprague-Dawley rats were housed in suspension cages and allowed free access to food and water. When a proper weight of 200 grams was attained, the animals received a 25% full thickness scald burn on the dorsum for 15 seconds, under diethyl ether anesthesia. The rats were then returned to their cages and fasted overnight, but allowed to drink tap water ad libitum. At the start of the three day study, the animals were randomized into one of the three groups to receive a 50 ml/day entral lipid emulsion containing 50 Kcal, 2 g amino acids (AA), and 40% nonprotein calories as lipids.

The details of the test and the results are shown in tables 1 to 8.

Liver protein synthesis (PS, umol leu g day) and liver fractional synthetic rate (FSR, % day) were estimated using a 4 hr. constant intravenous infusion of [1-14c] leucine on day 3.

Mean values for cumulative nitrogen balance (CNB, mgN/day 2 and 3), serum albumin (SA, g/dl), liver fractional synthetic rates (FSR) and liver protein synthesis (PS) are summarized in the table below:

| | CNB | Albumin | Liver FSR | Liver PS |
|---|---|---|---|---|
| LCT | $-12 + 9$ | $2.2 + .1$ | $31 + 3$ | 41.5 |
| MCT | $-29 + 20$ | $2.9 + .1$ | $29 + 2$ | $39 + 3$ |
| SL | $56 + 21$ | $2.9 + .2$ | $52 + 4$ | $74 + 7$ |

The structural lipid of this invention showed greater cumulative nitrogen balance, liver fractional synthetic rate andliver protein synthesis than the long chain triglyceride or the medium chain triglyceride.

These data show that the enteral use of the structured lipid has significant nutritional advantages over the enteral use or conventional lipids in cases of severe metabolic stress.

Figure 2:
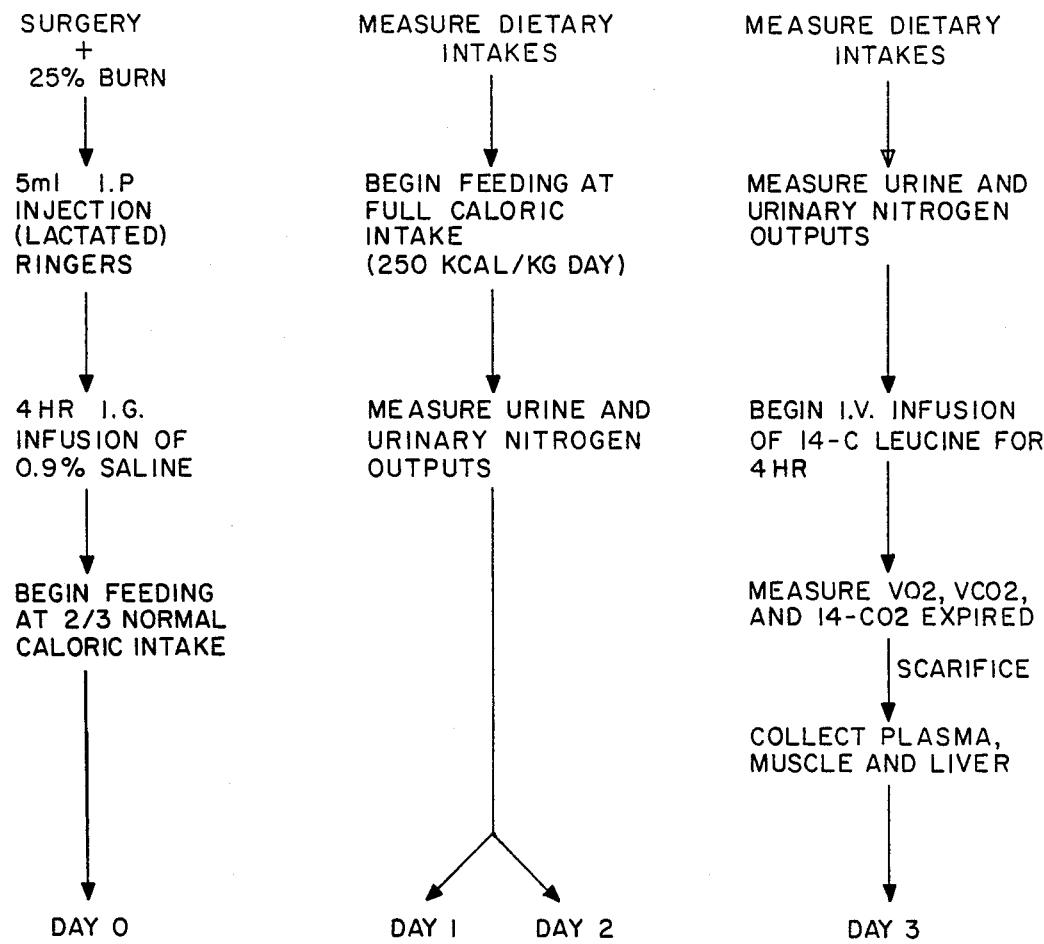
FIG. 2 is an Experimental Protocol for Example II.

The experimental protocol is shown in FIG. 2.

TABLE 1

Composition of enteral lipid emulsions.

| | Soybean LCT* | Medium chain triglyceride Captex 300* | Structured triglyceride 710A* |
|---|---|---|---|
| oil (g/L) | 200 | 200 | 200 |
| egg yolk phospholipid (g/L) | 12 | 12 | 12 |
| glycerol (g/L) | 25 | 25 | 25 |
| water (g/L) | 763 | 763 | 763 |
| approximate pH** | 7.8 | 7.8 | 7.8 |

20% lipid emulsions were prepared using a Gaulin Homogenizer employing six passes at a second stage/first stage pressure of 500/5000 (psi).
*Capital City Products, Columbus, Ohio
**pH adjusted with 0.1 NaOH

TABLE 2

Dietary Intake of Experimental Groups.
250 kcal/kg/day

| | Total caloric Intake (kcal/kg/day) | Protein Intake (gAA/kg/day) | Nonprotein Calories (% dextrose) | Nonprotein Calories (% lipid) |
|---|---|---|---|---|
| Group I (AA, dextrose and LCT*) | 250 | 9.8 | 60 | 40 |
| Group II (AA, dextrose and MCT**) | 250 | 9.8 | 60 | 40 |
| Group III (AA, dextrose and 710A) | 250 | 9.8 | 60 | 40 |

*LCT = Long chain triglyceride
**MCT = Medium chain triglyceride

TABLE 3

Composition of Enteral Diets (250 kcal/kg/day)

| | |
|---|---|
| amino acids (g/l)* | 39.0 |
| dextrose (g/l) | 148.2 |
| lipid (g/l) | 37.3 |
| Additives | |
| sodium chloride (mEq/l) | 30 |
| sodium acetate (mEq/l) | 30 |
| potassium chloride (mEq/l) | 30 |
| potassium acetate (mEq/l) | 25 |
| potassium phosphate (mEq/l) | 15 |
| calcium gluconate (mEq/l) | 8 |
| magnesium sulfate (mEq/l) | 8 |
| trace mineral mix (ml/l)** | 8 |
| choline chloride (mg/l) | 300 |
| multivitamin concentrate (ml/l)*** | 5 |

*crystalline amino acids (Travasol, Baxter-Travenol Laboratories, Deerfield, IL);
**trace mineral mix (Ascot Pharmaceuticals, Inc., Skokie, IL);
***multivitamin concentrate (M.V.C. 9 + 3, Lyphomed, Inc., Melrose Park, IL);
Trace mineral mix (mg/l): zinc chloride, 16.7; cupric chloride, 8.6; manganese chloride, 2.9; chromic chloride, 0.2; selenious acid, 0.3
Multivitamin concentrate (per liter): ascorbic acid, 50 mg; retinol, 1650 IU; ergocalciferol, 100 IU; Thiamine, 1.5 mg; riboflavin, 1.8 mg; pyridoxine, 2.0 mg; niacinamide 20 mg; dexpanthenol, 7.5 mg; dl-alpha-tocopherol acetate, 5 IU; biotin, 30 ug; folic acid, 200 ug, cyanocobalamin, 2.5 ug

TABLE 4

Survival of burned rats after 3 days of enteral feeding.

| Diet | Caloric Intake (kcal/kg/day) | Surviving Rats/ total no. of rats | % Survival |
|---|---|---|---|
| Group I (AA, dextrose and LCT*) | 250 | 12/12 | 100 |
| Group II (AA, dextrose and MCT**) | 250 | 8/8 | 100 |
| Group III (AA, dextrose and 710A) | 250 | 7/7 | 100 |

*LCT = Long chain triglyceride
**MCT = Medium chain triglyceride

TABLE 5

Effect of thermal injury on body weight change and nitrogen metabolism in rats.

| Group | n | Change in body weight (g/3 days) | Nitrogen balance (mg/day) Day 0 | Day 1 | Day 2 | Cumulative nitrogen balance (mg/day 2 + 3) |
|---|---|---|---|---|---|---|
| LCT | 12 | −13.9 ± 1.6 | −119 ± 9 | −5 ± 6 | −7 ± 6 | −12 ± 9 |
| MCT | 8 | −15.1 ± 1.2 | −124 ± 17 | −17 ± 11 | −11 ± 10 | −29 ± 20 |
| Structured lipid (710A) | 8 | −12.1 ± 1.8 | −112 ± 16 | 19 ± 14 | 37 ± 10* | 56 ± 21 a,b |

Values are means ± SE
n = number of rats
*P < 0.01, structured lipid vs MCT and LCT
a = P < 0.05, structured lipid vs LCT
b = P < 0.01, structured lipid vs MCT

TABLE 6

Metabolic parameters in burned rats after 3 days of enteral feeding.

| | LCT | MCT | Structured lipid (710A) |
|---|---|---|---|
| Plasma leucine, umol/ml | 0.159 ± 0.008 (9) | 0.165 ± 0.007 (8) | 0.146 ± 0.006 (7) |
| Respiratory quotient | 1.02 ± 0.01 (10) | 0.99 ± 0.01 (8) | 1.05 ± 0.02 (8) |
| Oxygen consumption, umol/100 g/hr | 4973 ± 312 (10) | 4856 ± 287 (8) | 5475 ± 562 (8) |
| Total energy expenditure, kcal/kg/day | 134 ± 8 (10) | 130 ± 8 (8) | 149 ± 15 (8) |
| Liver protein (%) | 18.3 ± 0.4 (9) | 18.6 ± 0.3 (8) | 19.4 ± 0.3 (7) |
| Muscle protein (%) | 17.2 ± 0.2 (9) | 16.2 ± 0.1 (8) | 16.4 ± 0.2 (7) |
| Serum albumin, g/dl | 2.2 ± 0.1 (10)* | 2.9 ± 0.04 (8) | 2.9 ± 0.2 (7)* |

Values are means ± SE
Parentheses indicate number of rats
*P < 0.01, LCT vs MCT

TABLE 7

Muscle and liver fractional synthetic rates (FSR) and protein synthesis in enterally fed burned rats.

| Group | n | Muscle FSR (%/day) | Muscle Protein synthesis | Liver FSR (%/day) | Liver Protein synthesis |
|---|---|---|---|---|---|
| LCT | 9 | 2.4 ± 0.1 | 2.6 ± 0.2 | 31.1 ± 3.4 | 41.4 ± 4.7 |
| MCT | 8 | 2.6 ± 0.1 | 2.6 ± 0.1 | 28.8 ± 1.7 | 38.8 ± 2.5 |
| Structured lipid | 7 | 3.0 ± 0.3 | 3.1 ± 0.3 | 52.3 ± 4.5*** | 73.7 ± 7.2* |

TABLE 7-continued

Muscle and liver fractional synthetic rates (FSR) and protein synthesis in enterally fed burned rats.

| Group | n | Muscle FSR (%/day) | Muscle Protein synthesis | Liver FSR (%/day) | Liver Protein synthesis |
|---|---|---|---|---|---|
| (710A) | | | | | |

Values are means ± SE
n = number of rats
a = (umol leucine/g/day)
***P < 0.01, structured lipid vs MCT and LCT

TABLE 8

| Group | (n) | Dietary intake | Release from protein | Appearance | Incorporation into protein | Oxidation |
|---|---|---|---|---|---|---|
| | | | umol leucine/hr/100 g | | | |
| LCT | 9 | 17.4 ± 1.1 | 17.5 ± 1.1 | 34.9 ± 2.2 | 26.1 ± 1.9 | 8.8 ± 0.7 |
| MCT | 8 | 17.3 ± 0.9 | 17.7 ± 1.1 | 35.0 ± 2.0 | 26.1 ± 1.7 | 8.9 ± 0.7 |
| Structured lipid (710A) | 7 | 17.4 ± 1.0 | 16.2 ± 0.8 | 33.5 ± 1.8 | 23.9 ± 0.8 | 9.6 ± 1.3 |

Values are means ± SE
n = number of rats

What is claimed is:

1. A method of preventing catabolism and increasing protein synthesis in a subject undergoing metabolic stress, which comprises administering enterally to the subject from about 0.3 gms of fat/Kg of body weight/day to about 4.0 gms of fat/Kg of body weight/day of a synthetic structured lipid of the formula

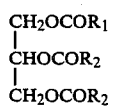

wherein $R_1$ and $R_2$ may be independently a $C_6$ to $C_{24}$ acid provided that one of $R_1$, $R_2$ or $R_3$ is a $C_{12}$ acid, and one of $R_1$, $R_2$ and $R_3$ is omega 6 or omega 3 acid.

2. The method according to claim 1 wherein the synthetic structured lipid is a rearranged mixture of a kernel type oil rich in fatty acids $C_6$-$C_{12}$ and long chain triglycerides (LCT) oils having a percent composition of MCT to LCT 70 to 30%, 80 to 20%, 85 to 15% or 90 to 10%.

3. The method according to claim 2 wherein the percent composition of MCT to LCT is 80 to 20% or 85 to 15%.

4. The method according to claim 2 wherein the structured lipid comprises a medium chain triglyceride having a high lauric acid content and the long chain triglyceride has a high polyunsaturated acid content.

5. The method according to claim 4 wherein the medium chain triglyceride oils are babassu oil, coconut oil, cohune oil, palm kernel oil, tucum oil, and fractions thereof, and the long chain triglyceride oils are corn oil, peanut oil, safflower oil, soybean oil, sunflower seed oil and fish oil.

6. The method according to claim 5 wherein the structured lipid is prepared from a fractionated palm kernel oil and soybean oil.

7. The method according to claim 5 wherein the structured lipid is prepared from a mixture of 80% coconut oil and 20% soybean oil.

8. A pharmaceutical composition for enteral administration in preventing catabolism and increasing protein synthesis in a subject undergoing metabolic stress which comprises a structured lipid of the formula

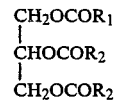

wherein $R_1$ and $R_2$ may be independently a $C_6$ to $C_{24}$ acid provided that one of $R_1$, $R_2$ or $R_3$ is a $C_{12}$ acid, and one of $R_1$, $R_2$ and $R_3$ is omega 6 or omega 3 acid.

9. The pharmaceutical composition according to claim 8 wherein the structured lipid is prepared from a medium chain triglyceride oil having a high lauric acid content and a long chain triglyceride oil having a high polyunsaturated acid content.

10. The pharmaceutical composition according to claim 8 wherein the medium chain triglyceride oils are babassu oil, coconut oil, cohune oil, palm kernel oil, tucum oil, and fractions thereof, and the long chain triglyceride oils and corn oil, peanut oil, safflower oil, soybean oil, sunflower seed oil and fish oil.

11. The pharmaceutical composition according to claim 10 wherein the structured lipid is prepared from a fractionated palm kernel oil and soybean oil.

12. The pharmaceutical composition according to claim 10 wherein the structured lipid is prepared from a mixture of 80% coconut oil and 20% soybean oil.

13. The pharmaceutical composition according to claim 12 containing amino acids, vitamins and minerals in amounts effective for the treatment of the stressed subject.

* * * * *